United States Patent [19]

Holtkamp

[11] Patent Number: Plant 5,494

[45] Date of Patent: Jun. 18, 1985

[54] AFRICAN VIOLET PLANT NAMED SABRINA

[75] Inventor: Reinhold Holtkamp, Isselburg, Fed. Rep. of Germany

[73] Assignee: Gessellschaftsvertrag uber die Erfindergemeinschaft "Optimara", Rees Hafen, Fed. Rep. of Germany

[21] Appl. No.: 535,395

[22] Filed: Sep. 23, 1983

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet named Sabrina characterized by its red-purple flowers carried on upright flower stems, with the bouquet being compact and positioned centrally above the foliage, its compact growth habit, and its continuous flowering habit.

1 Drawing Figure

1

The present invention comprises a new and distinct cultivar of African violet plant, botanically known as *Saintpaulia ionantha,* and named Sabrina.

Sabrina is a sport of the cultivar Arizona, disclosed in my U.S. Plant Pat. No. 4,374, granted Feb. 6, 1979. The new cultivar was discovered from a block of flowering plants of the parent cultivar grown in a cultivated area in Nashville, Tenn. Subsequent asexual reproduction of the new cultivar by leaf cuttings, as performed by me at Nashville, Tenn., has demonstrated that the combination of characteristics as herein disclosed for the new cultivar are firmly fixed and are retained through successive generations of asexual reproduction.

Sabrina has not been observed under all possible environmental conditions. The phenotype may vary significantly with variations in environment such as temperature, light intensity and day length. The following observations, measurements and values describe the new cultivar as grown in Isselburg, West Germany and Nashville, Tenn., under greenhouse conditions which closely approximate those generally used in commercial practice.

The following traits have been repeatedly observed and are determined to be basic characteristics of Sabrina, which in combination distinguish this African violet as a new and distinct cultivar:

(1) Compact growth habit.

(2) Seven to nine upright and wire-like flower stems, each of which supports 7–12 flowers, thereby providing a very compact and floriferous flower head.

(3) The center of each flower petal frequently contains a thin stripe of somewhat lighter flower color.

(4) The flower petals are flexible, thereby inhibiting premature dropping of the flowers.

(5) When compared to the parent cultivar Arizona, Sabrina has a much lighter red-purple flower color perceptively pink in nature, as opposed to the more reddish flowers of the parent cultivar, and by its slightly lighter foliage color. Sabrina is a continuous flowering cultivar.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately 2:00 P.M. in early September in Nashville, Tenn.

2

Botanical classification: *Saintpaulia ionantha,* Ramat. cv. SABRINA

Parentage:

A sport of the cultivar Arizona, disclosed in U.S. Plant Pat. No. 4,374.

Propagation: The new cultivar holds its distinguishing characteristics through successive propagations by leaf cuttings and by division of shoots.

Plant: From 6 cm. to 8 cm. tall when grown in pots, and approximately 20 cm. in diameter when fully grown.

*Leaves.*—General form: Heart shape, serrated. Diameter: 50–55 mm. Texture: Velvet. Aspect: Hairy. Veins: Visable, well pronounced on underside. Color (upperside): Yellow green, 147A. Color (underside): Greenish, purplish red. Petiole: Brownish purple, hairy.

*Flowers.*—Buds: Bell shaped; 9–12 buds and more. Sepals: Spear shaped, hairy, brownish when immature. Color: Red-purple 68A-B. Peduncle: Brownish green, hairy, wiry.

*Individual flowers.*—Size: 35 mm. Color: Upperside: Red-purple 68A-B. Underside: Red purple 65A-B. Borne: On 7–9 or more upright and wire-like stems. Shape: Violet shaped, single. Corolla: Upright. Flowering time: 8–10 weeks after potting a fully developed flower bouquet is formed.

*Reproductive organs.*—Anthers: Two anther cells. Filaments: Purplish-green. Styles: Intensive purple with white tip; ovary is light green and hairy, with the seed capsule pushing slightly through the flower.

*Roots.*—White when young and active, and brownish green when older.

*Disease resistance.*—Good resistance against any known disease.

General observations: Sabrina is a highly floriferous variety, having 7–12 flowers carried on each of 7–9 upright flower stems. A highly floriferous bouquet is formed well above the pleasantly contrasting relatively dark green foliage, and the variety flowers continuously.

I claim:

1. A new and distinct cultivar of African violet plant named Sabrina, as described and illustrated, and particularly characterized by its red-purple flowers carried on upright flower stems, with the bouquet being compact and positioned centrally above the foliage, its compact growth habit, and its continuous flowering habit.

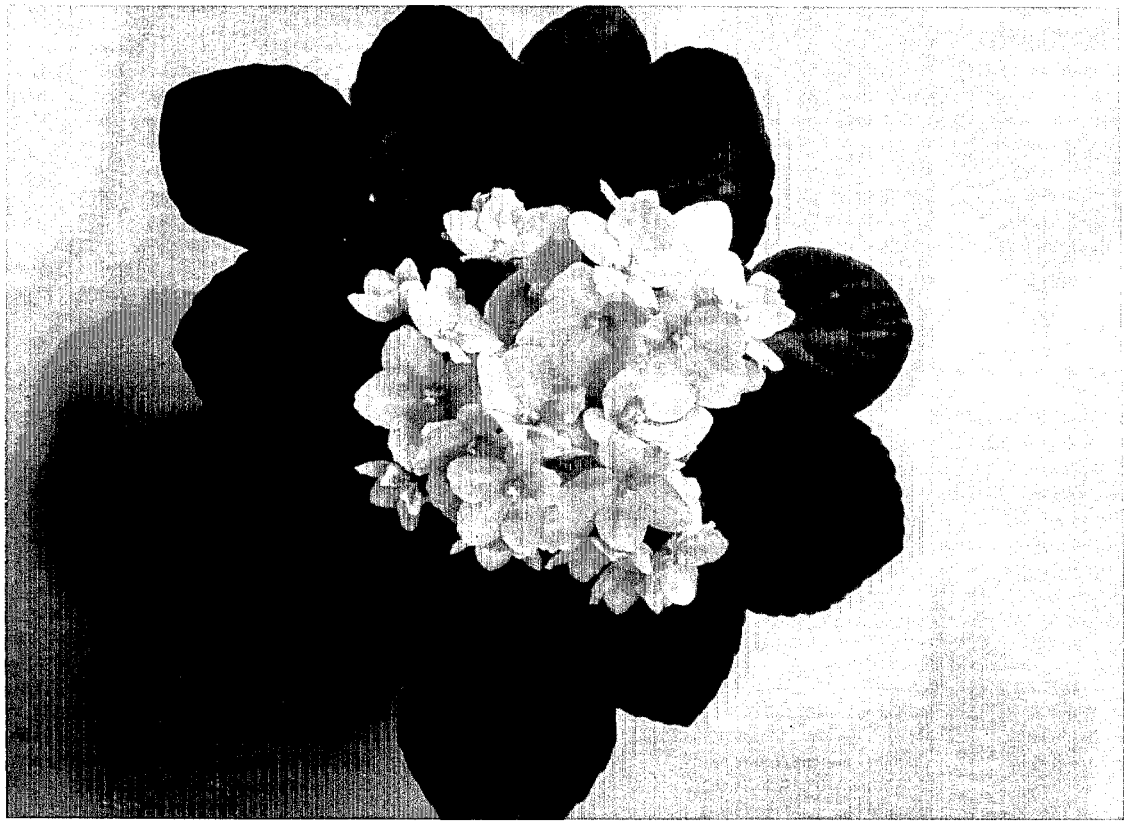

* * * * *